United States Patent [19]

Bluestein

[11] 4,111,973

[45] Sep. 5, 1978

[54] PROCESS FOR PRODUCING A CYCLOTRISILOXANE IN A CRACKING REACTION

[75] Inventor: Ben A. Bluestein, Schenectady, N.Y.

[73] Assignee: General Electric Company, Waterford, N.Y.

[21] Appl. No.: 856,425

[22] Filed: Dec. 1, 1977

[51] Int. Cl.² .............................................. C07F 7/08
[52] U.S. Cl. ............................................. 260/448.2 E
[58] Field of Search ................................. 260/448.2 E

[56] References Cited

U.S. PATENT DOCUMENTS

| | | | |
|---|---|---|---|
| 2,961,425 | 11/1960 | Pierce et al. | 260/46.5 R |
| 2,979,519 | 4/1961 | Pierce et al. | 260/448.2 E |
| 3,002,951 | 10/1961 | Johannson | 260/46.5 R |
| 3,179,619 | 4/1965 | Brown | 260/37 R |
| 3,989,733 | 11/1976 | Okamoto et al. | 260/448.2 E |

*Primary Examiner*—Paul F. Shaver
*Attorney, Agent, or Firm*—E. Philip Koltos; John L. Young; Frank L. Neuhauser

[57] ABSTRACT

An improved process for increasing the yield and purity of fluoroalkyl cyclotrisiloxanes in a cracking reaction of diorganopolysiloxanes by using, in addition to the cracking catalyst, an effective amount of a higher aliphatic alcohol having from 14 to 30 carbon atoms. By the use of such a higher aliphatic alcohol, there is consistently obtained yields of high purity fluoroalkyl cyclotrisiloxanes from cracking reactions of silicone hydrolyzates in excess of 80% by weight.

16 Claims, No Drawings

PROCESS FOR PRODUCING A CYCLOTRISILOXANE IN A CRACKING REACTION

BACKGROUND OF THE INVENTION

The present invention relates to a cracking process of diorganopolysiloxanes to produce a cyclotrisiloxane therefrom and more particularly the present invention relates to the above cracking process where there is incorporated along with the reactants an effective amount of a higher aliphatic alcohol so that the yield of cyclotrisiloxane of improved purity from the cracking process is over 90% by weight and is obtained at a faster rate. Heat cured silicone rubber compositions are well known in the silicone art. Such heat cured compositions comprise a linear diorganopolysiloxane polymer having a viscosity varying from 1,000,000 to 200,000,000 centipoise at 25° C. where the organo groups are selected from monovalent hydrocarbon radicals and halogenated monovalent hydrocarbon radicals, extending or reinforcing fillers such as silica, lithopone, zinc oxide, etc. pigments, heat aging additives, flame retardant additives, vulcanizing agents and various other additives.

Such heat curable silicone compositions are cured by incorporating into them an organic peroxide, which upon heating the composition at temperatures above 100° C. results in a silicone elastomer. Silicone oils are also well known in that they comprise linear diorganopolysiloxane polymers of a viscosity of anywhere from 50 to 100,000 centipoise at 25° C. Various other additives may be added to the composition.

There have also been developed room temperature vulcanizable silicone rubber compositions wherein the main ingredient is silanol terminated diorganopolysiloxane polymer having a viscosity varying anywhere from 1,000 to 500,000 centipoise at 25° C. where the organo groups are selected from monovalent hydrocarbon radicals and halogenated monovalent hydrocarbon radicals. Such compositions include various ingredients in them besides the silanol fluid, such as adhesion promoters, the extending and reinforcing fillers, cross-linking agent such as methyltriacetoxysilane or methyltrimethoxy silane and catalysts such as a metal salt of a carboxylic acid. These compositions cure to a silicone elastomer at room temperature upon being exposed to atmospheric moisture.

Also, there have been developed silicon hydride olefin platinum catalyzed silicone rubber compositions which comprise vinyl terminated diorganopolysiloxane polymers of a viscosity varying from 1,000 to 200,000,000 centipoise at 25° C.; silicon hydrides containing polysiloxane or silicone resin; and a platinum catalyst. Such compositions when all the components are mixed together will cure at room temperature over an extended period of time or in a matter of a minute at temperatures above room temperature to a silicone elastomer.

The most basic ingredient in any of these compositions, is a linear diorganopolysiloxane polymer, which may have any of the viscosities mentioned above. Accordingly, the process for producing such linear diorganopolysiloxane polymers is one that has merited a great deal of attention. For most organo groups in such polymers, that is where the organo groups are selected from lower alkyl such as methyl, ethyl, propyl and vinyl. Such processes for producing such linear diorganopolysiloxane polymers comprise first adding diorganodihalogensilanes to water. Such diorganodichlorosilanes may contain up to 10% of trifunctional silane units or monofunctional silane units. The resulting diorganodichlorosilanes when added to water hydrolyze to form a mixture of cyclic siloxanes, that is cyclotrisiloxanes and cyclotetrasiloxanes and up to cyclosiloxanes containing 10 or more siloxy units. The silicone hydrolyzate mixture also contains low molecular weight silanol terminated diorganopolysiloxanes where the number of diorganosiloxy units is repeated anywhere from 1 to 30 times.

Such a silicone hydrolyzate is of little use by itself to form any of the foregoing polymers mentioned previously. Accordingly, it is common in the silicone industry to take such a silicone hydrolyzate and add to it an alkali metal hydroxide at a concentration of anywhere from 5 to 500 parts per million of the silicone hydrolyzate. The alkali metal hydroxide normally being potassium hydroxide. The mixture is then heated at elevated temperatures above 100° or 150° C. so as to convert most of the silicone hydrolyzate to distilled cyclotetrasiloxanes; such cyclotetrasiloxanes being the desired ingredient for the preparation of linear diorganopolysiloxane polymers. It is also known that if the hydrolyzate is carefully fractionated during the heating process, then cyclotrisiloxane can be distilled off during such a cracking process and most of the hydrolyzate will be converted to the cyclotrisiloxane. However, if the cyclotrisiloxane is not removed and the silicone hydrolyzate is heated and distilled rapidly, then most of the silicone hydrolyzate will be converted to cyclotetrasiloxanes. Such cyclotetrasiloxanes can be mixed with cyclotetrasiloxanes substituted by other organic groups, if desired, which siloxanes are produced by the same cracking reaction and the resulting mixture equilibrated at temperatures above 100° or 150° C. and preferably below 150° C. in the presence of an alkali metal hydroxide catalyst preferably potassium hydroxide, which is desirably present at a concentration of 5 to 500 parts per million to convert most of the cyclotetrasiloxanes to a linear diorganopolysiloxane polymer.

There is also included in such a reaction mixture the appropriate amount of chainstoppers such as hexamethyldisiloxane or divinyltetramethyldisiloxane or other triorganosiloxy endstopped diorganopolysiloxanes of low molecular weight so as to chainstop the linear diorganopolysiloxane polymer. The amount of chainstoppers generally determine the ultimate or average molecular weight of the linear diorganopolysiloxane polymers that is formed. It should be noted that during such a reaction the most conversion of the linear diorganopolysiloxane from the cyclotetrasiloxanes is obtained is when 85% (in the case of a dimethyl substituted siloxane) of the cyclotetrasiloxanes have been converted to the linear diorganopolysiloxane polymer. When this 85% equilibrium point has been reached or approached, it is common to neutralize the basic catalyst in the reaction mixture and vent off the remaining cyclotetrasiloxanes to yield the pure diorganopolysiloxane polymer.

It should be noted that in the case of low molecular weight linear diorganopolysiloxane polymers that are formed the equilibration reaction is carried out in the presence of acid catalysts such as, toluenesulfonic acid.

In the production of low molecular weight linear diorganopolysiloxanes, it is common to use an acid catalyst while in the production of higher viscosity diorganopolysiloxane polymers it is more practical to use strong basic catalysts.

As can be appreciated from the above, the cracking reaction for forming the maximum amount of cyclotetrasiloxanes is very important in the formation of such linear diorganopolysiloxane polymers.

It should also be noted that the production of fluorine substituted linear polysiloxane polymers are important in producing any of the above polymer compositions, the advantage of fluorine substituted linear polysiloxane polymers being to prepare solvent-resistant silicone elastomers. However, the formation of fluorine or fluoroalkyl substituted linear polysiloxane polymers proceeds within an equilibration reaction utilizing a cyclotrisiloxane instead of the traditional cyclotetrasiloxanes; for instance see the disclosures of U.S. Pat. No. 2,961,425 and U.S. Pat. No. 2,979,519, U.S. Pat. No. 3,002,951 and U.S. Pat. No. 3,179,619.

In fluorosilicone chemistry, the process for forming fluoroalkyl substituted siloxanes comprises hydrolyzing fluoroalkyldichlorosilanes, adding an alkali metal catalyst to the fluorosilicone hydrolyzate and cracking the mixture at elevated temperatures of above 100° and more preferably at reduced pressures and continuously during such cracking reaction stripping off cyclotrisiloxanes as they are formed. By stripping off the cyclotrisiloxanes as they are formed, the yield of the cyclotrisiloxanes from the silicone hydrolyzate is maximized. In accordance with this process, it is possible to obtain 80% conversion of the silicone hydrolyzate to cyclotrisiloxanes and some times even as high as 90% or more by weight of the silicone hydrolyzate. The cyclotrisiloxanes are then equilibrated with the appropriate amount of chainstoppers with a basic catalyst as disclosed in the foregoing patents to obtain the desired molecular weight linear fluoroalkyl substituted polysiloxane polymer at about 100% conversion of the cyclotrisiloxanes to the linear polymer. Then the catalyst is neutralized and the linear polymer can be utilized in production of fluorosilicone compositions.

It should be noted that there are other processes for producing linear fluorosilicone polymers from cyclotetrasiloxanes, such as for instance those disclosed in U.S. Pat. No. 3,997,496 and U.S. Pat. No. 3,937,684 of John S. Razzano which are hereby incorporated into the present case by reference. However, these fluorosilicone cyclotetrasiloxanes when they are reacted in an equilibration reaction produce above 60% yield of the linear polymer but below 100% since such a process is not as efficient for the production of fluorosilicone polymers as is the case of the cyclotrisiloxanes.

Accordingly, to maximize the efficiency and to minimize the cost of the production of fluorosilicone composition, it is necessary to maximize the efficiency of the cracking reaction so as to obtain the maximum amount of cyclotrisiloxane from the cracking reaction of the fluorosilicone hydrolyzate, since in the equilibration step where 100% of the cyclotrisiloxane is converted to the linear polymer, it is not seen that part of the process can be maximized any further. However, in the process of producing the fluorosilicone cyclotrisiloxane by the cracking of the silicone hydrolyzate with a basic catalyst, it has been found normally that as high a yield of the cyclotrisiloxane is not obtained as could be desired. Accordingly, yields of 80% and sometimes as high as 90% have been achieved if the process conditions were followed meticulously. However, in many cases, there is only obtained 70% yields or less and in addition, the cyclotrisiloxane, that is obtained has a small amount of impurities in it which are undesirable in the finished silicone elastomer. Since such impurities are liquids and soluble they cannot be filtered out. In addition, when the silicone hydrolyzate when 70% of it or more has been converted to the cyclotrisiloxane the residue has the tendency to brown and gel, thus becoming unusable. In addition, many times a strong objectionable odor is imparted to the cyclotrisiloxanes that are distilled in the cracking reaction which odor has yet been unidentified.

Accordingly, it is highly desirable in the production of fluorosilicone polymers to maximize the yield and rate of formation of cyclotrisiloxanes from the cracking reaction of the silicone hydrolyzate and to minimize the amount of the impurities that may be distilled over with the cyclotrisiloxane.

Accordingly, it is one object of the present invention to provide for an efficient process for producing fluoroalkyl cyclotrisiloxanes.

It is an additonal object of the present invention to provide for an improved process for producing fluoroalkyl cyclotrisiloxanes by using in addition to the cracking catalyst an effective amount of a higher alcohol.

It is another object of the present invention to provide for an improved process for producing fluoralkyl cyclotrisiloxanes at a yield of more than 80% or more in the cracking reaction of the silicone hydrolyzate.

It is yet an additional object of the present invention to provide for an improved process for producing fluoroalkyl cyclotrisiloxanes from silicone hydrolyzates where the cyclotrisiloxanes have very few impurities in it. These and other objects of the present invention are accomplished by means of the disclosure set forth hereinbelow.

SUMMARY OF THE INVENTION

In accordance with the above objects there is provided by the present invention a process for improving the yield and purity of cylcotrisiloxanes of the formula,

(R R' Si O)$_3$ where R is selected from the class consisting of an alkyl radical of 1 to 8 carbon atoms and alkenyl radicals of 2 to 8 carbon atoms and R' is a fluoralkyl radical of 3 to 8 carbon atoms comprising adding to a diorganodihalosilane hydrolyzate an effective amount of an alkali metal hydroxide, and an effective amount of an additive selected from the class consisting of aliphatic alcohol and salts of aliphatic alcohols wherein such additives have from 14 to 30 carbon atoms and where the organo groups of the diorganodihalosilane are the same as R and R' and heating the resulting mixture to make and remove the cyclotrisiloxane. The preferred cyclotrisiloxane that is formed is methyl 3,3,3 trifluoropropylcyclotrisiloxane. The diorganodihalosilane hydrolyzate is obtained by taking a diorganodichlorosilane and adding that to sufficient water to completely hydrolyze the chlorine groups then removing the excess water and hydrochloric acid that is formed during the reaction. This silicone hydrolyzate is then taken and there is added to it appropriate amounts of the alkali metal hydroxide catalyst and an effective amount of the higher alcohol and the reaction mixture is heated above 100° C. and more desirably between 120° and 300° C. and so as to distill off preferentially cyclotrisiloxanes.

By the use of this process, there is obtained a cyclotrisiloxane in yields of 80% or more in most cases if the reaction is completed consistently from the silicone hydrolyzate. The alkali metal hydroxide catalyst is preferably selected from the class consisting of potassium hydroxide, sodium hydroxide, lithium hydroxide and cesium hydroxide. The preferred catalyst is sodium hydroxide since potassium and cesium hydroxide tend to be a little strong and the lithium hydroxide tends to be a little weak, although they can be used. The alkali metal hydroxide is generally used at a concentration of 0.01 to 10% by weight of the hydrolyzate while the alcohol is generally added at a concentration varying from 0.5 to 30% by weight of the hydrolyzate and more preferably from 1 to 5% by weight of the hydrolyzate. The most preferred alcohol is octadecanol. It should be noted that generally the reaction temperature can be anywhere from 120° to 300° C. and is more preferably 120° C. to 250° C. at pressures of 5 millimeters to 100 millimeters of mercury. It has been found that by the utilization of such higher alcohols, the alcohol ingredients can be utilized for more than one silicone hydrolyzate batch, that is the alcohols of the instant case can be utilized with one or two or as much as three silicone hydrolyzate batches to continuously distill off cyclotrisiloxanes at a high yield.

It also should be noted that it is desired to add the cracking catalyst for ease of dispersion, as a high solids aqueous solution to the silicone hyrolyzate.

DESCRIPTION OF THE PREFERRED EMBODIMENT

It should be noted first of all that the improved process in the cracking reaction of diorganodihalosilane hydrolyzate is only found to take place in processes for the production of fluoroalkyl substituted cyclotrisiloxanes. It may be that the instant improved process will not operate with diphenyl or phenyl containing cyclotrisiloxanes.

Accordingly, the instant improved process is limited to a cracking process where alkyl, fluoroalkyl substituted cyclotrisiloxanes are obtained from hydrolyzates and mixtures of polysiloxanes containing alkyl, fluoroalkyl substituted siloxanes. The R radical in the above formula of the cyclotrisiloxane can be selected from any alkyl radical of 1 to 8 carbon atoms such as methyl, ethyl, propyl and cycloalkyl radicals of up to 8 carbon atoms such as cyclohexyl, cycloheptyl, etc. alkenyl radicals of 1 to 8 carbon atoms and the radical R' is preferably selected from a fluoroalkyl radical from 3 to 8 carbon atoms, the most preferred substituents for the R radical being methyl, ethyl or vinyl. Accordingly, the instant process applies only to diorganodihalosilanes hydrolyzate and mixtures of cyclopolysiloxanes where the organo groups in such diorganodihalosilane hydrolyzate are the same as that identified for the R and R' radicals of the cyclotrisiloxane formula that is discussed above.

In the initial part of the process in the instant case, the diorganodihalosilane and spcifically the diorganodichlorosilane reactants are taken and hydrolyzed in water by simply pouring them into a water bath and then obtaining the foregoing hydrolyzate wherein the chlorine of the halogen groups are hydrolyzed to substitute oxygen atoms from the chlorine atoms. It should be noted that the preferred halogen in the diorganodihalosilane reactants is chlorine. A solvent may be added to the hydrolysis mixture to ease the separation out of the siloxanes that are formed. However, such is not necessary since the silicone hydrolyzate layer will be separated out from the water layer as the hydrolyzate is formed. It should be noted that excess water creates no problem in the foregoing hydrolysis since the water can easily be removed by well-known decantation or separation techniques. An excess amount of water is desirable in the foregoing hydrolysis since it will dissolve the hydrogen chloride by-product that is formed from the reaction and facilitate the purifying of the silicone hydrolyzate.

At this point the silicone hydrolyzate may be washed with various amounts of water so as to remove all the acid from the hydrolyzate. It is preferred that this reaction be carried out at room temperature. However, higher reaction temperatures may be utilized.

Accordingly, and preferably, the hydrolysis of the diorganodichlorosilane takes place in a water bath with or without solvent at room temperature. The silicone hydrolyzate may then be washed several times with water or mild aqueous base, such as sodium bicarbonate, to remove any excess acid present in the hydrolyzate. In addition, temperatures of 40°-50° C. may be utilized in the reaction so as to permit faster separation of the desired product. The preferable way to carry out the hydrolysis reaction is to hydrolyze the diorganodichlorosilanes in water and remove the water phase of the hydrolysis mixture and then wash the silicone hydrolyzate several times so as to remove all excess acid.

The silicone hydrolyzate that is formed, then consists of cyclic siloxanes with most of the cyclic siloxanes being cyclotrisiloxanes and cyclotetrasiloxanes and with a certain amount of low and higher molecular weight silanol end-stopped diorganopolysiloxanes. If a solvent is present then the solvent can be removed by heating the reaction mixture under a vacuum so as to strip off the solvent.

The diorganodichlorosilane hydrolyzate is then taken and placed in the reaction chamber. To this there must be added an effective amount of an alkali metal hydroxide cracking catalyst. The known cracking catalyst for such a cracking reaction of the diorganodichlorosilane hydrolyzate are for instance potassium hydroxide, sodium hydroxide and cesium hydroxide. There may also be used as a cracking catalyst the reaction product of such alkali metal hydroxide catalyst with cyclic siloxanes or low molecular weight linear diorganopolysiloxane polymers. Such catalysts which are known as alkali metal silanolates can be produced insitu during the reaction when the alkali metal hydroxide is added to the silicone hydrolyzate or there may be produced prior to the cracking reaction. Generally, it is preferred to add the alkali metal hydroxide to the diorganodichlorosilane hydrolyzate and allow the alkali metal silanolate to form insitu during the cracking reaction.

It should be also noted that the diorganodichlorosilanes that are added to the water to form a hydrolyzate may contain up to 10% by weight of monoorganotrichlorosilanes and triorganochlorosilanes. However, it is preferred in the instant process that the diorganodichlorosilane be as pure as possible and contain less than 0.5% by weight of these other chlorosilanes. If the presence of these other chlorosilanes is too high, then the yield of the cyclotrisiloxane in the cracking process is reduced and further these materials interfere with the cracking process and may result in premature gelling of the hydrolyzate and in an impure cyclotrisiloxane.

It should also be noted with respect to the alkali metal hydroxide catalyst that the most preferred catalyst is sodium hydroxide. Lithium hydroxide catalyst is not as strong as would be desired and as a result the yield is not maximized as much as possible. In the case of the potassium or cesium hydroxide, such hydroxide catalyst is a little too strong and in some cases when it is utilized in cracking reaction results in the hydroxide attacking the silicone hydrolyzate and degrading it to form gel particles and other undesirable by-products in the reaction system. Accordingly, although all of the above catalysts may be used, the one other than Na OH reduce the purity and yield somewhat.

In addition, in accordance with the instant disclosure there is needed to be added to the silicone hydrolyzate an effective amount of the alkali metal hydroxide catalyst. Accordingly, this may constitute a concentration of alkali metal hydroxide of anywhere from 0.01 to 10% by weight of the silicone hydrolyzate. Preferably it has been found desirable to utilize from 0.1 to 1% by weight of the alkali metal hydroxide catalyst. If less than 0.01% is utilized, the reaction is extremely slow during the cracking process and if more than 10% of the weight of the alkali metal hydroxide is utilized then the excess amount of alkali metal hydroxide may attack the silicone hydrolyzate causing some degradation of the components of the silicone hydrolyzate and thus reducing the desired amount of yield from the cracking process.

It is desirable to add the alkali metal hydroxide as an aqueous solution to the silicone hydrolyzate. If it is added as a solid by itself, then it is hard to disperse in the silicone hydrolyzate. If it is added as a solution in methanol or a lower aliphatic alcohol then the alcohol may distill or react with the cyclictrisiloxane that is obtained and may contaminate such cyclictrisiloxane thus requiring additional purification procedures. However, the aqueous solutions of the alkali metal hydroxide are easily handled and dispersed into the silicone hydrolyzate. It should be noted that when such aqueous systems of the alkali metal hydroxide are utilized, then the excess water is removed by placing a vacuum over the hydrolyzate reaction chamber as soon as the aqueous solution of the alkali metal hydroxide is added and removing the water so that the water will not interfere with the cracking reaction of the process. Generally, it is preferred that the aqueous alkali metal hydroxide solution be added to the silicone hydrolyzate wherein the aqueous alkali metal hydroxide is present in the concentration of 10 to 50% by weight in the aqueous solution. It is more preferred that the aqueous solution contain from 30 to 40% by weight of alkali metal hydroxide since there is less water to remove in that case. In the most preferred process it is desired to utilize from 0.1 to 1% by weight of the alkali metal hydroxide based on the silicone hydrolyzate since this concentration of alkali metal hydroxide results in lower reaction times and the most effective use of the hydroxide in forming the desired cyclictrisiloxanes without degrading or attacking the silicone hydrolyzate.

In addition to the alkali metal hydroxide there must be added in an effective amount to the cracking reaction mixture the stabilizing additive of the instant case. Such stabilizing additive must be one that has a boiling point of above 250° to 300° C. so that it will stay in the reaction pot and will not distill over with the cyclotrisiloxane, thus not contaminating the cyclotrisiloxane in one aspect and in another aspect being present in the cracking reaction chamber so as to preserve its function of stabilizing the formation of a cyclotrisiloxane product.

Accordingly, most aliphatic alcohols having a total carbon atom content of anywhere from 14 to 30 carbon atoms will operate in the instant invention. This includes not only saturated aliphatic alcohols of 14 to 30 carbon atoms, but also includes aliphatic alcohols having aliphatic unsaturation of 14 to 30 carbon atoms. It is also possible that the salts of the foregoing aliphatic alcohols may be utilized as a stabilizing additive in the instant process. In fact it is postulated that alkali metal hydroxide salts of such aliphatic alcohols may be formed after the stabilizing additive is added to the cracking reaction mixture which salts somehow stabilize the formation of a cyclictrisiloxane and prevent the formation of impurities such as unwanted by-products in browning or gelling of the silicone hydrolyzate that is present in the cracking reaction vessel.

It should be noted that glycols and polyethers will not operate in the instant process, since they decompose at the high temperatures needed for the instant process. Further, the alcohols must necessarily not be halogenated since at the high temperature of the reaction the halogen groups might react with the alkali metal hydroxide, thus forming unwanted by-products and not allowing the alkali-metal hydroxide to perform its catalytic function in the cracking process. Aromatics such as phenols are also undesirable since many of them do not have a high enough boiling point and also such alcohols tend to be acidic which is undesired in the instant cracking process.

Accordingly, it is desirable to use aliphatic alcohols and salts of alcohols as mentioned previously wherein the boiling point of such alcohols is above at least 250° C. and more preferably above 300° C. The stabilizing additive may be added to the reaction mixture at only an effective amount of concentration, that is at concentrations in the neighborhood of 0.1% by weight or less. However, while such concentration of the alcohol will affect some stabilizing properties to the cracking reaction mixture, it is highly desirable that it be utilized at a concentration of 0.5% to anywhere up to 30% by weight of the silicone hydrolyzate. It should be noted that it is not altogether desirable to use concentrations of up to 30% by weight since this make the process more expensive. The most preferred concentration range for the aliphatic alcohol stabilizing additive in the cracking reaction of the instant case is at a concentration of 1 to 5% by weight of the silicone hydrolyzate. It should also be noted that a concentration of less than 0.5% by weight the alcohol does not have as effective a stabilizing effect upon the cracking reaction as would be desired, and that concentrations of 30% or more may be undesirable in that the excess alcohol serves no suitable function in the cracking process of the instant case. Accordingly, the preferred concentration of 1 to 5% by weight based on the silicone hydrolyzate, is the preferred concentration to be utilized in most cracking processes.

The alcohol need not be added in a solvent solution. Normally it may be a solid at room temperature and can be added as such and dispersed in the cracking reaction mixture since the alcohol will dissolve or disperse into the silicone hydrolyzate upon increasing the temperature of the reaction mixture above 100° since the alcohol will form a liquid and be easily dispersed into the silicone hydrolyzate. Again a solution in solvents such as acetone may be utilized of such aliphatic alcohols which are utilized as stabilizing additives of the instant case. However, if such is done the solvent should be removed by distillation from the reaction mixture prior to the onset of the cracking reaction. Also, there is the problem of disposing of the used solvent.

Accordingly, it is most preferred that a stabilizing, solid additive aliphatic alcohol or salt of an aliphatic alcohol be added to the cracking reaction mixture as a solid an allowed to melt and disperse with agitation in the silicone hydrolyzate that is being subjected to the cracking reaction.

With these ingredients present in the cracking reaction chamber then it is only necessary to increase the temperature to above 100° C. so as to initiate the cracking reaction. It should be noted that at this point during such cracking reaction if the cyclotrisiloxane is continually distilled most of the silicone hydrolyzate is converted to a cyclotrisiloxane. However, if cyclotrisiloxane is not distilled and allowed to remain in the cracking reaction pot, then most of the siloxane product that will be formed will be a cyclotetrasiloxane. Accordingly, since in the instant process it is preferred to produce cyclotrisiloxanes, there is continually distilled and obtained as an overhead product, the cyclotrisiloxane of the instant invention.

To carry out the reaction of the instant process under the reaction conditions, it is desired that the temperature be maintained in the range of anywhere of 120°-300° C. or above at atmospheric pressure or below atmospheric pressure. The preferred temperature range for the cracking reaction of the instant invention is the temperature of 120°-250° C. under pressure of 5 millimeters to 100 millimeters of mercury. Unduly high temperatures are not desired, such as temperatures above 300° C. since they might effect degradation of the silicone hydrolyzate or the desired product.

Accordingly, it is desired that the temperature of 300° C. be not exceeded in the cracking process of the instant case. In another vein, a temperature of less than 120° or 100° C. would result in the reaction in the cracking process proceeding very slowly and would require very low pressure and thus resulting in an uneconomic use of processing facilities. The best reaction temperature for the process of the instant case is the preferred reaction temperature of anywhere from 120° to 250° C. at 5 millimeters to 100 millimeters of mercury. The methyltrifluoropropyl cyclotrisiloxane which is the preferred tricyclotrisiloxane of the instant case has a boiling point at 17 millimeters of mercury of anywhere from 128° to 131° C.

Accordingly, by utilizing a reduced pressure in carrying out the cracking reaction of the instant process, there is obtained overhead cyclotrisiloxanes without degrading the aliphatic alcohol or exceeding its boiling temperature and without causing any undue degradation of the organic substituents of the silicone hydrolyzate. The reaction times for such a cracking process as that of the instant case may vary from 3 to 48 hours or more preferably from 3 to 8 hours. The instant reaction period will be a function of the amount and type of alkali metal hydroxide catalyst used as well as the reaction temperature. Accordingly, with the milder sodium hydroxide catalyst versus the potassium hydroxide, there is less degradation of the silicone hydrolyzate and there is obtained at temperatures of 120° to 250° C. under vacuum the desired cyclotrisiloxane in the maximum yield.

Accordingly with the preferred reaction temperature and catalyst in the process of the instant case, there is obtained a yield of at least 90% by weight of the preferred cyclotrisiloxane of the instant case in a period of time of anywhere from 5 to 16 hours and more preferably a period of time of anywhere from 3 to 8 hours. When there is utilized in the instant process the stabilizing additive of the instant process of the instant case, there is obtained a yield of at least 80% in the instant case and yields of as high as 95% or above of the silicone hydrolyzate converted to the cyclotrisiloxane when the reaction is allowed to go to completion. Such yields are obtained with no browning or gelling of the silicone hydrolyzate and without the formation of large amounts of impurities which are distilled over the cyclotrisiloxane and also without the cyclotrisiloxane having any objectionable odors as was the case with the processes of the prior art.

It should also be noted that the preferred alcohol for utilizing as a stabilizing additive in the cracking process of the instant case is octadecanol. It has been found in various experiments that it works satisfactorily in accordance with the above disclosure. However, examples of other high boiling alcohols that may be utilized are as follows: hexadecanol, oleyl alcohol, heptadecanol, phytol and 2-nonadecanol.

It should be understood that the alcohols of the instant disclosure for stabilizing additives for the instant process are not limited to the above alcohols, but may include any aliphatic alcohol that has a sufficiently high boiling point and is stable material at a temperatures of up to 250° C. or 300° C. or above, at atmospheric pressure. It should be noted that it is preferred that the cracking process of the instant case be carried out under reduced pressure since lower cracking temperatures may be utilized in the reaction vessel thus avoiding as much as possible the degradation of the silicone hydrolyzate during the cracking reaction or the degradation of the stabilizing additive, that is the aliphatic alcohol as slight as it might be.

At this point of the process, the cyclotrisiloxane which is obtained at high yields is then ready to be utilized to form a fluorosilicone polymer. Generally, such cyclotrisiloxane it taken in substantially pure form and there is added to it in the case of low molecular weight oils, from 1 to 5% by weight of a mild acid, such as toluene sulfonic acid. There is also added to the mixture the desired amount of chainstoppers that is, hexamethyldisiloxane, divinyltetramethyldisiloxane, and other low molecular weight linear siloxanes which are trimethylsiloxy endstopped having from 1 to 30 repeating siloxy units. Another catalyst that can be utilized in such an equilibration reaction is acid activated clay, specifically, sulfuric acid activated clay such as Filtrol sold by the Filtrol Corporation of Los Angeles, Calif. The resulting mixtures are equilibrated or heated at temperatures above 100° C. and more preferably above 150° C. to produce the desired linear fluorosilicone polymer of the desired molecular weight. The end point of such equilibration reaction is reached when most of the cyclicsiloxanes have been converted to the linear polymer. At that point the acid catalyst is neutralized with a mild base such as ammonium hydroxide and the linear fluoroalkyl substituted polysiloxane is ready to be utilized as an oil or to form various compositions. It should be noted that in the foregoing process there may be utilized as chainstopper silanol endstopped low molecular weight polysiloxane polymers. When such a chainstopper is utilized then there is obtained a silanol terminated linear fluoroalkyl polysiloxane polymer. Utilizing such a procedure fluorosilicone polymers may be obtained having a viscosity of anywhere from 1,000 to 200,000,000 centipoise at 25° C. The preparation of the linear diorganopolysiloxane polymers which are fluoroalkyl substituted to produce heat curable silicone rubber compositions, is much the same as the above except alkali metal hydroxide catalysts are utilized.

Accordingly, for the production of high viscosity fluorosilicone linear polymers, the fluoroalkyl cyclotrisiloxane is placed in the reaction vessel and there is added the appropriate concentration of the triorganosiloxy endstopped linear diorganopolysiloxane polymers of low molecular weight. To this reaction mixture there is added the appropriate amount of alkali metal hydroxide catalyst. With respect to the catalyst, any of the alkali metal hydroxide catalysts can be utilized in the equilibration reaction. The preferred catalyst is either a potassium hydroxide or sodium hydroxide. However, it should be noted that there also can be utilized alkali metal silanolates which can be either formed in situ in the reaction mixture or can be preformed. As such, alkali metal silanolates will work with the desired efficiency in the equilibration reaction and they have the advantages that they can be easily dispersed into the cyclotrisiloxane reaction ingredient.

It should be noted that the more desired catalysts, when high molecular weight diorganopolysiloxane polymers are to be formed from the cyclotrisiloxanes are potassium hydroxide and potassium silanolates. Such catalsts effect the conversion of the cyclotrisiloxanes to a very high molecular weight polymer, that is polymers having a viscosity in excess of 50,000,000 centipoise at 25° C. and up to as high as 300,000,000 centipoise at 25° C. Such alkali metal hydroxide catalysts can be utilized generally at a concentration of 5–500 parts per million of the cyclotrisiloxane and more preferably at concentrations of anywhere from 10 to 100 parts per million based on the cyclotrisiloxane. The reaction mixture is then heated at temperatures above 50° C. and more preferably above 100° C. at atmospheric pressure to obtain the desired fluoroalkyl substituted linear polysiloxane polymer having a viscosity of anywhere from 1,000,000 to 300,000,000 centipoise at 25° C. It should be noted that in the foregoing equilibration process of the cyclotrisiloxanes, that about 100% of the cyclotrisiloxanes are converted to the linear fluoroalkyl substituted polysiloxane polymer. Accordingly, in this process of producing fluoroalkyl substituted linear polysiloxane polymers, there is obtained the maximum conversion or optimum conversion of the cyclotrisiloxanes into the linear polymer. After the conversion of the cyclotrisiloxanes to the linear polymer, the temperature is reduced to room temperature and there is added to the reaction mixture sufficient amounts of mild acids to neutralize the basic catalyst that is present. Examples of acid neutralizing agents to neutralize the basic catalyst are for instance carbon dioxide hydrogen chloride, acetic acid, phosphoric acid, etc. To produce a heat curable silicone rubber composition from such a polymer, there is incorporated into the polymer anywhere from 5 to 150 parts by weight per hundred parts of the polymer of an extending or reinforcing fillers or mixtures of such fillers. Examples of the reinforcing filler that can be utilized with a polymer of the instant case are for instance fumed silica, precipitated silica, mixtures of such silicas. It is preferred in many cases that the filler be treated so as to prevent the phenomena known as crepe hardening of the uncured fluorosilicone composition. Examples of treating agents that may be utilized with fumed silica or precipitated silica are for instance cyclic siloxanes such as octamethylcyclotetrasiloxane and silazanes.

Examples of extending fillers that may be utilized or added to the fluorosilicone polymer are for instance lithopone, diatomaceous earth, zinc oxide, glass fibers, aluminum silicate, quartz, etc. Another necessary ingredient in the polymer of the instant case is a process aid, which is preferably a silanol terminated process aid or nitrogen functional process aid. Such process aids are desired in heat curable silicone rubber compositions so as to prevent the uncured composition from structuring prior to cure and to facilitate the mixing of the filler into the polymer. There may be added various additives to the uncured composition along with the filler such as flame retardant additives such as carbon black and platinum alone or in combination with heat aging additives, self-bonding additives, etc.

Finally, after all the ingredients are mixed into the composition, the composition may then be stored or sold as such to a heat curable silicone rubber formulator. The formulator will then take the uncured silicone rubber composition add to it a peroxide curing catalyst where there is present anywhere from 0.01 to 10% by weight of the peroxide curing catalysts based on the total weight of the composition, mill or extrude the composition to the desired shape and heat the composition at temperatures above 100° C. so as to decompose the peroxide catalyst and cause the cure of the uncured composition to a silicone elastomer, such a silicon elastomer not only has the properties of most elastomers but also has enhanced solvent resistance to organic solvents such as jet fuels.

With respect to specifics of producing fluoroalkyl substituted heat curable silicone rubber compositions, the foregoing patents mentioned previously disclose such compositions. In addition, most of the well-known additives in non-fluoro containing heat curable silicone rubber compositions can be utilized with fluorosilicone heat curable silicone rubber composition. In accordance with the improved cracking process of the instant case, there can be obtained with advantage at an optimum yield of fluoroalkyl substituted cyclotrisiloxanes which are highly desirable in the production of fluorine substituted polymers and fluorine substituted heat curable silicone rubber compositions.

Examples below are given for the purpose of illustrating the reduction to practice of the instant invention. The examples are not given for any purpose of setting limits or defining the scope to the instant invention. All parts in the examples are by weight.

EXAMPLE I

A trifluoropropylmethylsiloxane hydrolyzate, 75 pts. and 0.75 pts. (1%) of solid potassium hydroxide was placed in a flask attached to an 18" - helice - packed column. About 53 pts. of material was distilled. The distillation temperature was below 145° at 17 mm. Hg pressure, during 4.5 hours. The distillate comprised 83% cyclic tetramer. After continued heating of about 1.5 hr., the contents of the distilling flask became brown and much brown solids were noted at the end of the distillation. The yield was 71%.

EXAMPLE II

When the experiment above was repeated, except that 1.8 pts. (2.2%) octadecanol was included in the charge, then 22 pts of distillate was obtained in the first 1.5 hours and the contents of the pot were only lightly colored and less solids were noted. this experiment was terminated prematurely.

EXAMPLE III

In an experiment similar to the above, but with a charge of 200 pts. of fluoropropylsiloxanes hydrolyzate, 1.0 pts. (0.5%) of potassium hydroxide and 6 pts. (3%) of octadecanol and using a large diameter Todd column, 145 pts. of distillate (b.p. 128°–129°/17 mm. of Hg over 98% timer) was obtained in 6 hours. The residue was light yellow and only traces of odors were noted. The yield was 72%, although reaction was not allowed to go to completion.

EXAMPLE IV

To 125 pts. of fluoropropylsiloxanes was added a solution of 0.25 pts. (0.2%) sodium hydroxide in water. Using a small Todd column 17 pts. of distillate (below 141°/17 mm. of Hg. was obtained in 1.7 hr. An additional 1.0 pts. (0.8%) sodium hydroxide was added, and then 27 pts. of distillate was obtained in the next 2 hours. White chunks of solid were noted towards the end of the distillation. The color was a light yellow. The yield was 22%, since the reaction was not allowed to go to completion.

EXAMPLE V

In another experiment using a larger Todd column, 300 pts. of fluoropropylsiloxanes hydrolyzate were prestripped to remove the cyclic trimmer already present. To the remaining 170 pts. was added 1.7 pts. sodium hydroxide in methanol. 19 pts. of trimer (b.p. 128°–131°/17 mm. of Hg. was obtained in 37 minutes and much gel was noted in the pot. When 5 pts. (3%) octadecanol was added to the pot, an additional 54 pts. of trimer was distilled in 3 hours. The gel was still present. Yield from the first reaction was 6% after the addition of the alcohol, the yield was 22%.

EXAMPLE VI

To 200 pts. of fluoropropylsiloxanes, 0.4 pts. (0.2%) sodium hydroxide and 4 pts. (2%) octadecanol were reacted in the same equipment as in Example II. In 3.8 hours, 125 pts. of cyclic trimer was obtained. No gel was noted and the residue was a hazy, lightly colored fluid. No decomposition odors were detected. The yield was 62%, but the reaction was not allowed to go to completion.

EXAMPLE VII

A cracking run, similar to that Example VI, but using 3.0 pts. (1.5%) sodium hydroxide and 15 pts. (7.5%) octadecanol gave 137 pts. of cyclic trimer in 6.3 hours. The residue was cloudy and light yellow. The yield was 68%, but the reaction was not allowed to go to completion.

EXAMPLE VIII

To the residue from Example VII above was added an additional 239 pts. of fluoropropylsiloxane hydrolyzate. Continued cracking gave 141 pts. of trimer in 4.6 hr. A cloudy, light yellow residue, with some grainy particles, remained. The second yield was 59%, but the reaction was not allowed to go to completion.

The above experiments in Examples I–VIII were made at an early stage in the experimentation. The following Examples illustrate experiments at a more advanced state of the development of the invention.

EXAMPLES IX–XVIII

The cracking runs, Examples IX through XVII, Table I, were all done in the same manner. The designated weights of reagents were placed in a flask attached to a Todd fractionating column, and heated under vacuum. The distillates, boiling at about 128°–131° C. at 17 mm. Hg pressure, were collected as the cyclic trimer of trifluoropropylmethylsiloxane. They were analyzed by gas chromatography to determine their purity. The yields of the cyclic trimer (greater than 99% purity), the time taken to distill the material, and comments about the quality are given in Table I. All amounts are given in parts by weight.

TABLE I
EXAMPLES IX-XVIII

| Example No. | Fluoropropylsiloxane hydrolyzate | Catalyst | Promoter and/or Solvent | Trimer Yield | Distill. Time | Remarks |
|---|---|---|---|---|---|---|
| IX | 350 pt. | 1.5pt.KOH in 3.4pt.H$_2$O | None | 90% | 7.5 hr. | Odor and impurities in product. Gel in residue. |
| X | 350 pt. | 1.5pt.KOH in 3.4pt.H$_2$O | 10.5 pt. octadecanol | 83% | 10 hr. | Less impurities in product. Less Gel in residue. |
| XI | 350 pt. | 1.0pt.NaOH in 2.5pt.H$_2$O | None | 78% | 12 hr. | No odor or impurities in product. Residue fluid. |
| XII | 250 pt. | 0.5pt.NaOH in 1.2pt.H$_2$O | 2.5 pt. octadecanol | 87% | 8 hr. | No odor or impurities in product. Residue fluid. |
| XIII | 250 pt. | 1.2pt.NaOH in 7pt.methanol | 2.5 pt. octadecanol | 83% | 8 hr. | No odor or impurities in product. Residue fluid. |
| XIV | 250 pt. | 0.5pt.NaOH solid | 7.5 pt. octadecanol | 86% | 11 hr. | No odor or impurities in product. Residue fluid. |
| XV | 250 pt. | 1.2pt.NaOH in 7pt.methanol | 7.5 pt. oleylalcohol | 83% | 6 hr. | No odor or impurities in product. Residue fluid. |
| XVI | 250 pt. | 1.2pt.NaOH in 7pt.methanol | 7.5 pt. Carbowax 550 | 57% | 5.5 hr. | Product impure - Tars in residue. |
| XVII | 300 pt. | 1.8pt.NaOH in 9.2pt.H$_2$O | 7.5 pt. octadecene | 39% | 3 hr. | Reaction slowed down and stopped. |
| XVIII | 300 pt. | 1.8pt.NaOH in 4.2pt.H$_2$O | 7.5 pt. octadecene plus 9 pt.octadecanol | 82% | 10 hr. | No impurities in product. Residue fluid. |

What is claimed is:

1. A process for improving the yield and purity of a cyclotrisiloxane of the formula, (R R' Si O)$_3$ where R is selected from the class consisting of an alkyl radical of 1 to 8 carbon atoms cycloalkyl radicals of up to 8 carbon atoms and alkenyl radicals of 2 to 8 carbon atoms and R' is a fluoroalkyl radical of 3 to 8 carbon atoms comprising adding to a diorganodihalosilane hydrolyzate or a mixture of cyclopolysiloxanes, an effective amount of an alkali metal hydroxide, and an effective amount of a promoting additive selected from the class consisting of aliphatic alcohols, salts of aliphatic alcohols and aliphatic alcohols containing aliphatic unsaturation wherein such additives have from fourteen to thirty carbon atoms, where the organo groups are the same as R and R'; and heating the resulting mixture at a temperature above 100° C.

2. The process of claim 1 wherein the cyclotrisiloxane has the formula, (CH$_3$, CF$_3$CH$_2$CH$_2$SiO)$_3$.

3. The process of claim 1 wherein said diorganodihalosilane hydrolyzate is prepared by adding said diorganodihalosilanes to water where the halo is chlorine and separating the silicone hydrolyzate from the excess water and acid that is formed.

4. The process of claim 3 wherein said silicone hydrolyzate contains mixtures of cyclic siloxanes with the predominate cyclic siloxanes being the cyclotetrasiloxanes and cyclotrisiloxanes and wherein there is also present in the mixtures low and/or high molecular weight silanol terminated diorganopolysiloxanes.

5. The process of claim 1 wherein the alkali metal hydroxide is selected from the class consisting of KOH, Na OH, and Cs OH.

6. The process of claim 5 wherein the alkali metal hydroxide is present at a concentration of 0.01 to 10% by weight of the hydrolyzate.

7. The process of claim 6 wherein the alkali metal hydroxide is present at a concentration of 0.1 to 1% weight of the hydrolyzates.

8. The process of claim 1 wherein the heating temperature varies from 120° to 300° C. at lower than atmospheric pressure for a period of time varying from 3 to 48 hours.

9. The process of claim 8 wherein the heating temperature varies from 120° to 250° C. at a pressure varying from 5 mm. to 100 mm. of Hg. with a reaction period varying from 3 to 8 hours.

10. The process of claim 5 wherein the alkali metal hydroxide added to hydrolyzate is a 10% to 50% by weight of alkali metal hydroxide aqueous solution and wherein the water is removed by applying a vacuum over the hydrolyzate just prior to the heating step.

11. The process of claim 1 wherein the stabilizing additive is present at a concentration of 0.5 to 30% by weight of the hydrolyzate.

12. The process of claim 11 wherein the stabilizing additive is octadecanol and is present at a concentration of 1 to 5% by weight of the hydrolyzate.

13. The process of claim 1 wherein during said heating there is continually distilled overhead the cyclotrisiloxane in substantially pure form and at a yield of over 80%.

14. The process of claim 13 wherein after most of said hydrolyzate has been distilled over as the cyclotrisiloxane there is added additional hydrolyzate to the reaction vessel and the process is continued in a semi-continuous manner.

15. The process of claim 14 wherein two or three batches of silicone hydrolyzate can be processed with the same initial alkali metal hydroxide and stabilizing additive.

16. A process for improving the yield and purity of a cyclotrisiloxane of the formula, (R R' SiO)$_3$ where R is selected from the class consisting of an alkyl radical of 1 to 8 carbon atoms cycloalkyl radicals of up to 8 carbon atoms and alkenyl radicals of 2 to 8 carbon atoms and R' is a fluoroalkyl radical of 3 to 8 carbon atoms comprising (a) adding a diorganohalosilane to water where the organo is the same as R and R' and the halo is chlorine (b) separating the silicone hydrolyzate that is formed from excess water and acid by-products; (c) adding to said hydrolyzate from 0.01 to 10% by weight of the hydrolyzate of an alkali metal hydroxide selected from the class consisting of KOH, NaOH and Cs OH and from 0.5 to 30% by weight of the hydrolyzate of a stabilizing additive selected from the class consisting of aliphatic alcohols; salts of aliphatic alcohols and aliphatic alcohols containing aliphatic unsaturation wherein said additives have from fourteen to thirty carbon atoms, (d) heating the mixture at a temperature of from 120° to 250° C. at a pressure varying from 6 to 60 mm. of Hg. for a period of time varying from 3 to 48 hours; (e) continuously distilling overhead the substantially pure cyclotrisiloxane and obtaining said cyclotrisiloxane at yields of at least 80% by weight of said hydrolyzate and (f) adding additional hydrolyzate to the reaction mixture having the alkali metal hydroxide and stabilizing additive therein after the initial hydrolyzate has been depleted to semi-continuously recover the desired substantially pure cyclotrisiloxane.

* * * * *